(12) United States Patent
Elokdah

(10) Patent No.: US 7,291,639 B2
(45) Date of Patent: Nov. 6, 2007

(54) ARYLOXY-ACETIC ACID COMPOUNDS USEFUL AS INHIBITORS OF PLASMINOGEN ACTIVATOR INHIBITOR-1 (PAI-1)

(75) Inventor: Hassan Mahmoud Elokdah, Yardley, PA (US)

(73) Assignee: Wyeth, Madison, NJ (US)

(*) Notice: Subject to any disclaimer, the term of this patent is extended or adjusted under 35 U.S.C. 154(b) by 74 days.

(21) Appl. No.: 10/171,056

(22) Filed: Jun. 13, 2002

(65) Prior Publication Data

US 2003/0013732 A1 Jan. 16, 2003

Related U.S. Application Data

(60) Provisional application No. 60/299,659, filed on Jun. 20, 2001.

(51) Int. Cl.
*A61K 31/41* (2006.01)
*A61K 31/4745* (2006.01)
*A61K 31/343* (2006.01)

(52) U.S. Cl. ............... 514/382; 514/301; 514/302; 514/469

(58) Field of Classification Search ............ 514/378, 514/382, 469, 301, 302, 314, 443, 456, 394, 514/381, 415, 397
See application file for complete search history.

(56) References Cited

U.S. PATENT DOCUMENTS

| | | | | |
|---|---|---|---|---|
| 5,457,109 A | * | 10/1995 | Antonucci et al. | 514/253.1 |
| 5,610,153 A | * | 3/1997 | Buhlmayer et al. | 514/211.07 |
| 5,847,008 A | * | 12/1998 | Doebber et al. | 514/708 |
| 6,110,963 A | | 8/2000 | Malamas | |
| 6,136,794 A | * | 10/2000 | Cook et al. | 514/56 |
| 6,166,069 A | | 12/2000 | Malamas et al. | 514/469 |

(Continued)

FOREIGN PATENT DOCUMENTS

WO      WO 99/43651      9/1999

(Continued)

OTHER PUBLICATIONS

"Novel Benzofuran and Benzothiophen Biphenyls as Inhibitors of Protein Tyrosine Phosphatase 1B with Antihyperglycemic Properties", Malamas et al., Journal of Medicinal Chemistry, 2000, 43(7), 1293-1310.*

(Continued)

*Primary Examiner*—Brian Kwon
(74) *Attorney, Agent, or Firm*—Woodcock Washburn LLP

(57) ABSTRACT

This invention provides methods of inhibiting plasminogen activator inhibitor-1 (PAI-1) in a mammal, utilizing compounds of the formula:

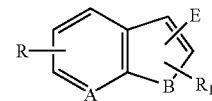

wherein: A is C or N; B is O, S, N, or CH=CH;

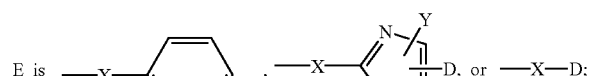

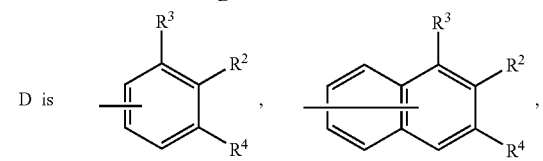

X is CO, CH(OH), $CH_2$, or —CH—S-2-benzothiazole; Y is H, alkyl, or halo; Z is O, S, or N;
R is H, nitro, alkyl, alkoxy, halo, or $CF_3$; $R^1$ is alkyl, aryl, aralkyl, halo, Het-alkyl, or optionally substituted aryl; Het is

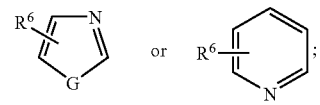

G is O, S, or N; $R^2$ is H, halo, alkyl, or —$OR^5$; $R^3$ and $R^4$ are H, halo, alkyl, aryl, nitro, amino, alkylsulfoamide, arylsulfoamide, cycloalkyl, heterocycle, or optionally substituted aryl; $R^5$ is H, alkyl, —$CH(R^7)R^8$, —$C(CH_2)_n CO_2R^9$, —$C(CH_3)_2CO_2R^9$, $CH(R^7)(CH_2)_n CO_2R^9$, or —$CH(R^7)C_6H_4CO_2R^9$; $R^6$ is alkylene; $R^7$ is H, alkyl, aryl, aralkyl, cycloalkyl, phthalic acid, or Q-alkyl;
Q is

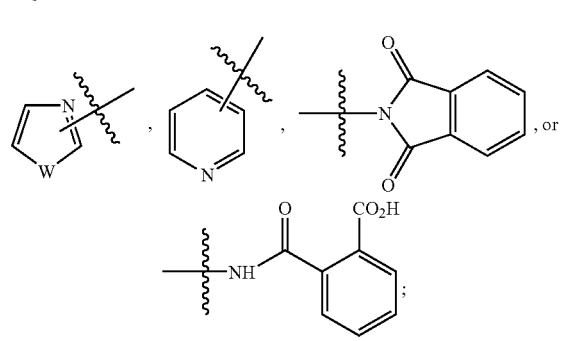

$R^8$ is —$CO_2R^{11}$, —$CONHR^{11}$, tetrazole, or —$PO_3R^{11}$; $R^9$ is H, alkyl, aryl, or aralkyl; W is O, N, or S; $R^{11}$ is H, alkyl, aryl, or aralkyl; n=1-6; or a pharmaceutically acceptable salt or ester form thereof.

12 Claims, No Drawings

U.S. PATENT DOCUMENTS

| | | | |
|---|---|---|---|
| 6,232,322 B1 | 5/2001 | Malamas et al. | 514/303 |
| 6,262,044 B1* | 7/2001 | M.o slashed.ller et al. | 514/202 |
| 6,369,072 B2 | 4/2002 | Malamas et al. | 514/301 |
| 6,391,897 B2 | 5/2002 | Malamas et al. | 514/310 |
| 6,509,360 B1 | 1/2003 | Malamas et al. | 514/339 |
| 6,589,970 B2* | 7/2003 | Commons et al. | 514/382 |
| 6,599,925 B2 | 7/2003 | Elokdah et al. | 514/378 |
| 6,599,929 B2 | 7/2003 | Cho et al. | 514/415 |
| 6,787,556 B1 | 9/2004 | Hargreaves et al. | 514/311 |
| 6,800,654 B2 | 10/2004 | Mayer et al. | 514/381 |
| 6,844,358 B2 | 1/2005 | Malamas et al. | 514/336 |
| 7,019,026 B1* | 3/2006 | Andersen et al. | 514/443 |
| 2003/0018067 A1 | 1/2003 | Elokdah et al. | 514/469 |
| 2003/0032626 A1 | 2/2003 | Mayer et al. | 514/79 |
| 2003/0125371 A1 | 7/2003 | Elokdah et al. | 514/419 |
| 2005/0070587 A1 | 3/2005 | Elokdah et al. | 514/381 |

FOREIGN PATENT DOCUMENTS

| | | |
|---|---|---|
| WO | WO 99/43672 | 9/1999 |
| WO | WO 99/58519 | 11/1999 |
| WO | WO 01/12187 | 2/2001 |
| WO | WO 03/031409 | 4/2003 |
| WO | WO 03/087087 | 10/2003 |

OTHER PUBLICATIONS

"Protein-Tyrosine Phosphatase !B (PTP1B): a Novel Therapetuic Target for Type 2 Diabletes Mellitus, Obesity and Related States of Insulin Resistance", Goldstein BJ, abstract, Curr Drug Targets Immune Endor Metabol Disord. Nov. 2001; 1(3):265-75.*

"Obestiy and INsulin Resistance", Kahn et al., J Clin Invest, Aug. 15, 2000; 106(4): 473-481.*

"NO Attenuates Insulin Signaling and Motility in Aortic Smooth Muscle Cells Via Protein Tyrosine Phosphatase !B-Meidated Mechanism", Sreejayan et al., Arterioscler Thromb Vasc Biol., 2002;22:1086-1092.*

"PTP-1B is an essential positive regulator of platelet integrin signaling", Arias-Salgado, JCB, vol. 170, No. 5, 2005.*

Paquet et al., Biochem. J., 1998, 333, pp. 591-599.*

Nordt et al., The Journal of Clinical Endocrinology & Metabolism, 85(4), 1563-1568 (2000).

Aznar et al., Haemostasis, 24, 243-251 (1994).

Carmeliet et al., Journal of Clinical Invest., 92, 2756-2760 (1993).

Daci et al., Journal of Bone & Mineral Research, 15(8), 1510-1516 (2000).

Biemond et al., Circulation, 91(4), 1175-1181 (1995).

Levi, et al., Circulation, 85(1), 305-312 (1992).

Rocha, et al., Fibrinolysis, 8, 294-303 (1994).

Reilly et al., Arteriosclerosis & Thrombosis 11, 1276-1286 (1991).

Krishnamurti et al., Blood, 69(3), 798-803 (1987).

Charlton, P., Expert Opinion on Investigational Drugs vol. 6, No. 5, pp. 539-554.

Malamas, M. S., et al., Journal of Medicinal Chemistry (2000) 43(7), 1293-1310.

Crandall, D. L. et al., "Characterization and comparative evaluation of a structurally unique PAI-1 inhibitor exhibiting oral in-vivo efficacy," *Journal of Thrombosis and Haemostasis*, Mar. 17, 2004, 2: 1-7.

* cited by examiner

ARYLOXY-ACETIC ACID COMPOUNDS USEFUL AS INHIBITORS OF PLASMINOGEN ACTIVATOR INHIBITOR-1 (PAI-1)

CROSS REFERENCE TO RELATED APPLICATIONS

This application claims priority to U.S. Provisional Application Ser. No. 60/299,659 filed Jun. 20, 2001.

This invention relates to methods of using aryloxy-acetic acid derivatives as inhibitors of plasminogen activator inhibitor-1 (PAI-1) for treating conditions resulting from fibrinolytic disorders such as deep vein thrombosis and coronary heart disease, and pulmonary fibrosis.

BACKGROUND OF INVENTION

Plasminogen activator inhibitor-1 (PAI-1) is a major regulatory component of the plasminogen-plasmin system. PAI-1 is the principal physiologic inhibitor of both tissue type plasminogen activator (t-PA) and urokinase type plasminogen activator (u-PA). Elevated plasma levels of PAI-1 have been associated with thrombotic events as indicated by animal experiments (Krishnamurti, *Blood,* 69, 798 (1987); Reilly, *Arteriosclerosis and Thrombosis,* 11, 1276 (1991); Carmeliet, *Journal of Clinical Investigation,* 92, 2756 (1993)) and clinical studies (Rocha, *Fibrinolysis,* 8, 294, 1994; Aznar, *Haemostasis* 24, 243 (1994)). Antibody neutralization of PAI-1 activity resulted in promotion of endogenous thrombolysis and reperfusion (Biemond, *Circulation,* 91, 1175 (1995); Levi, *Circulation* 85, 305, (1992)). Elevated levels of PAI-1 have also been implicated in diseases of women such as polycystic ovary syndrome (Nordt, *Journal of clinical Endocrinology and Metabolism,* 85, 4, 1563 (2000)) and bone loss induced by estrogen deficiency (Daci, *Journal of Bone and Mineral Research,* 15, 8, 1510 (2000)). Accordingly, agents that inhibit PAI-1 would be of utility in treating conditions originating from fibrinolytic disorder such as deep vein thrombosis, coronary heart disease, pulmonary fibrosis, polycystic ovary syndrome, etc.

U.S. Pat. No. 6,110,963 teaches aryloxy acetic acid derivatives of this invention as useful in the treatment of hyperglycemia.

SUMMARY OF THE INVENTION

This invention comprises methods of inhibiting plasminogen activator inhibitor-1 (PAI-1) in a mammal, preferably in a human, the methods comprising administering to a mammal in need thereof a pharmaceutically effective amount of a compound of the formula:

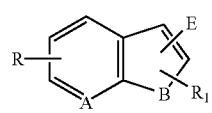

wherein
A is C or N;
B is O, S, N, or CH═CH;

E is 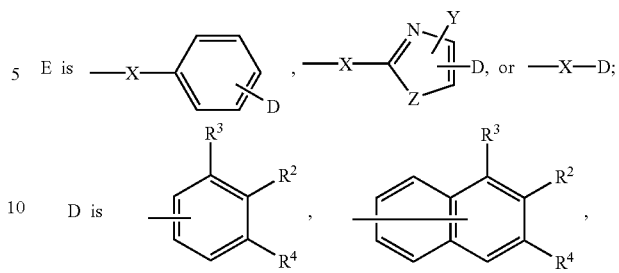

D is 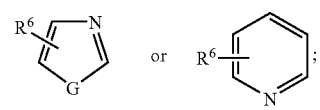

X is CO, CH(OH), CH$_2$, or —CH—S-2-benzothiazole;
Y is hydrogen, alkyl of 1-6 carbon atoms, or halogen;
Z is O, S, or N;
R is hydrogen, nitro, alkyl of 1-6 carbon atoms, alkoxy of 1-6 carbon atoms, halogen, or trifluoromethyl;
$R^1$ is alkyl of 1-12 carbon atoms, aryl of 6-10 carbon atoms, aralkyl of 7-15 carbon atoms, halogen, Het-alkyl wherein the alkyl moiety contains 1-6 carbon atoms, or aryl mono-, di- or tri-substituted with a substituent selected from the group consisting of halogen, alkyl of 1-6 carbon atoms, trifluoromethyl, and alkoxy of 1-6 carbon atoms;
Het is G is O, S, or N;
$R^2$ is hydrogen, halogen, alkyl of 1-6 carbon atoms, or —OR$^5$
$R^3$ and $R^4$ are each, independently, hydrogen, halogen, alkyl of 1-8 carbon atoms, aryl of 6-12 carbon atoms, nitro, amino, alkylsulfoamide, arylsulfoamide, cycloalkyl of 3-8 carbon atoms, heterocycle of 5 to 7 ring atom containing from 1 to 3 heteroatoms selected from oxygen, nitrogen, or sulfur, or aryl of 6-10 carbon atoms mono-, di- or tri-substituted with a substituent selected from the group consisting of halogen, alkyl of 1-6 carbon atoms, trifluoromethyl, alkoxy of 1-6 carbon atoms;
$R^5$ is hydrogen, alkyl of 1-6 carbon atoms, —CH(R$^7$)R$^8$, —C(CH$_2$)$_n$CO$_2$R$^9$, —C(CH$_3$)$_2$CO$_2$R$^9$, CH(R$^7$)(CH$_2$)$_n$CO$_2$R$^9$, or —CH(R$^7$)C$_6$H$_4$CO$_2$R$^9$;
$R^6$ is alkylene of 1-3 carbon atoms;
$R^7$ is hydrogen, alkyl of 1-6 carbon atoms, aryl of 6-12 carbon atoms, aralkyl of 6-12 carbon atoms, cycloalkyl of 3-8 carbon atoms, phthalic acid, or Q-alkyl wherein the alkyl moiety contains 1-6 carbon atoms;
Q is

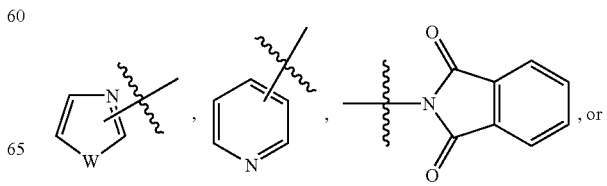

-continued

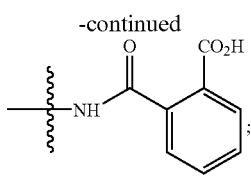

$R^8$ is $-CO_2R^{11}$, $-CONHR^{11}$, tetrazole, or $-PO_3R^{11}$;
$R^9$ is hydrogen, alkyl of 1-6 carbon atoms, aryl of 6-12 carbon atoms, or aralkyl of 7-15 carbon atoms;
W is O, N, or S;
$R^{11}$ is hydrogen, alkyl of 1-6 carbon atoms, aryl of 6-12 carbon atoms, or aralkyl of 7-15 carbon atoms;
n=1-6;

or a pharmaceutically acceptable salt or ester form thereof.

As used herein, alkyl includes both straight chain and branched alkyl moieties. Halogen means bromine, chlorine, fluorine, and iodine. It is preferred that the aryl portion of the aryl or aralkyl substituents herein is a phenyl, naphthyl or 1,4-benzodioxan-5-yl group; with phenyl being most preferred. The aryl moiety may be optionally mono-, di-, or tri-substituted with a substituent selected from the group consisting of alkyl of 1-6 carbon atoms, alkoxy of 1-6 carbon atoms, trifluoromethyl, halogen, alkoxycarbonyl of 2-7 carbon atoms, alkylamino of 1-6 carbon atoms, and dialkylamino in which each of the alkyl groups is of 1-6 carbon atoms, nitro, cyano, $-CO_2H$, alkylcarbonyloxy of 2-7 carbon atoms, and alkylcarbonyl of 2-7 carbon atoms.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

The compounds of the present invention are inhibitors of the serine protease inhibitor PAI-1, and are therefore useful in the treatment, inhibition, prevention or prophylaxis in a mammal, preferably in a human, of those processes which involve the production and/or action of PAI-1. Thus, the compounds of the invention are useful in the treatment or prevention of noninsulin dependent diabetes mellitus and cardiovascular disease caused by such condition, and prevention of thrombotic events associated with coronary artery and cerebrovascular disease. These compounds are also useful for inhibiting the disease process involving the thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery (such as joint replacement), and peripheral arterial occlusion. These compounds are also useful in treating stroke associated with or resulting from atrial fibrillation.

The compounds of the invention may also be used in the treatment of diseases associated with extracellular matrix accumulation, including, but not limited to, renal fibrosis, chronic obstructive pulmonary disease, polycystic ovary syndrome, restenosis, renovascular disease and organ transplant rejection.

The compounds of the invention may also be useful in the treatment of malignancies, and diseases associated with neoangiogenesis (such as diabetic retinopathy).

The compounds in the invention may also be used in conjunction with and following processes or procedures involving maintaining blood vessel patency, including vascular surgery, vascular graft and stent patency, organ, tissue and cell implantation and transplantation. The compounds in the invention may also be useful in the treatment of inflammatory diseases, septic shock and the vascular damage associated with infections.

The compounds of the invention are useful for the treatment of blood and blood products used in dialysis, blood storage in the fluid phase, especially ex vivo platelet aggregation. The present compounds may also be added to human plasma during the analysis of blood chemistry in hospital settings to determine the fibrinolytic capacity thereof.

The compounds in the present invention may also be used in combination with prothrombolytic, fibrinolytic and anticoagulant agents.

The compounds of the present invention may also be used to treat cancer including, but not limited to, breast and ovarian cancer, and as imaging agents for the identification of metastatic cancers.

The compounds of the invention may also be used in the treatment of Alzheimer's disease. This method may also be characterized as the inhibition of plasminogen activator by PAI-1 in a mammal, particularly a human, experiencing or subject to Alzheimer's disease. This method may also be characterized as a method of increasing or normalizing levels of plasmin concentration in a mammal, particularly those experiencing or subject to Alzheimer's disease.

The compounds of the invention may be used for the treatment of myelofibrosis with myeloid metaplasia by regulating stromal cell hyperplasia and increases in extracellular matrix proteins.

The compounds of the invention may also be used in conjunction with protease inhibitor-containing highly active antiretroviral therapy (HAART) for the treatment of diseases which originate from fibrinolytic impairment and hypercoagulability of HIV-1 infected patients receiving such therapy.

The compounds of the invention may be used for the treatment of diabetic nephropathy and renal dialysis associated with nephropathy.

The compounds of the invention may be used to treat cancer, septicemia, obesity, insulin resistance, proliferative diseases such as psoriasis, improving coagulation homeostasis, cerebrovascular diseases, microvascular disease, hypertension, dementia, osteoporosis, arthritis, asthma, heart failure, arrhythmia, angina, and as a hormone replacement agent, treating, preventing or reversing progression of atherosclerosis, Alzheimer's disease, osteoporosis, osteopenia; reducing inflammatory markers, reducing C-reactive protein, or preventing or treating low grade vascular inflammation, stroke, dementia, coronary heart disease, primary and secondary prevention of myocardial infarction, stable and unstable angina, primary prevention of coronary events, secondary prevention of cardiovascular events, peripheral vascular disease, peripheral arterial disease, acute vascular syndromes, reducing the risk of undergoing a myocardial revascularization procedure, microvascular diseases such as nephropathy, neuropathy, retinopathy and nephrotic syndrome, hypertension, Type 1 and 2 diabetes and related diseases, hyperglycemia, hyperinsulinemia, malignant lesions, premalignant lesions, gastrointestinal malignancies, liposarcomas and epithelial tumors, proliferative diseases such as psoriasis, improving coagulation homeostasis, and/or improving endothelial function, and all forms of cerebrovascular diseases.

The compounds of the invention may be used for the topical applications in wound healing for prevention of scarring.

This invention also comprises methods for the treatment, inhibition, prevention or prophylaxis in a mammal of each of the conditions or maladies listed herein. Each method comprises administering to a mammal in need thereof a pharmaceutically or therapeutically effective amount of a compound of this invention, or a pharmaceutically acceptable salt or ester form thereof.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Ester forms of the compounds of this invention include straight chain alkyl esters having from 1 to 6 carbon atoms or branched chain alkyl groups containing 3 or 6 carbon atoms, including methyl, ethyl, propyl, butyl, 2-methylpropyl and 1,1-dimethylethyl esters. Other esters useful with this invention include those of the formula —COOR$_{12}$ wherein R$_{12}$ is selected from the formulae:

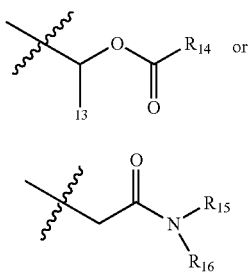

wherein R$_{13}$, R$_{14}$, R$_{15}$, and R$_{16}$, are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Among the preferred ester forms of the compounds herein include but not limited to C$_1$-C$_6$ alkyl esters, C$_3$-C$_6$ branched alkyl esters, benzyl esters, etc.

Among the preferred compounds of this invention are those of Formula I, in which:
A is C;
R is hydrogen;
R$^1$ is hydrogen, alkyl of 1-6 carbon atoms, or aralkyl of 7-15 carbon atoms; and
R$^3$ and R$^4$ are each, independently, hydrogen or halogen;

or a pharmaceutically acceptable salt thereof.

Specifically preferred compounds for use in the methods of the present invention include those set forth below:

6-[(2-butyl-benzofuran-3-yl)-hydroxy-methyl-naphthalen-2-ol;
6-[(2-butyl-benzofuran-3-ylmethyl)-naphthalen-2-ol;
1-bromo-6-(2-butyl-benzofuran-3-ylmethyl)-naphthalen-2-ol;
[1-bromo-6-(2-butyl-benzofuran-3-ylmethyl)-naphthalen-2-yloxy]-acetic acid;
2-[1-bromo-6-(2-butyl-benzofuran-3-ylmethyl)-naphthalen-2-yloxy]-3-phenyl-propionic acid;
5-[1-bromo-6-(2-butyl-benzofuran-3-ylmethyl)-naphthalen-2-yloxymethyl]-1H-tetrazole;
6-(2-butyl-benzofuran-3-ylmethyl)-1-iodo-naphthalen-2-ol;
2-[-6-(2-butyl-benzofuran-3-ylmethyl)-1-iodo-naphthalen-2-yloxy]-3-phenyl-propionic acid;
1-bromo-6-[(2-butyl-benzofuran-3-yl)-hydroxy-methyl]-naphthalen-2-ol;
[1-bromo-6-(2-butyl-benzofuran-3-carbonyl)-naphthalen-2-yloxy]-acetic acid;
2-[1-bromo-6-(2-butyl-benzofuran-3-carbonyl)-naphthalen-2-yloxy]-3-phenyl-propionic acid;
[5-bromo-6-(1H-tetrazol-5-ylmethoxy)-naphthalen-2-yl]-(2-butyl-benzofuran-3-yl)-methanone;
6-(2-benzyl-benzo[b]thiophen-3-ylmethyl)-1-bromo-naphthalen-2-ol;
4'-[(2-butyl-benzofuran-3-yl)-hydroxy-methyl]-biphenyl-4-ol;
(2-butyl-benzofuran-3-yl)-(4'-hydroxy-biphenyl-4-yl)-methanone;
4'-[(2-butyl-benzofuran-3-ylmethyl]-biphenyl-4-ol;
[4'-[(2-butyl-benzofuran-3-ylmethyl]-biphenyl-4-yloxy]-acetic acid;
5-[4'-(2-butyl-benzofuran-3-ylmethyl)-biphenyl-4-yloxymethyl]-1H-tetrazole;
{4'-[(2-butyl-benzofuran-3-yl)-hydroxy-methyl]-biphenyl-4-yloxy}-acetic acid;
3,5-dibromo-4'-[(2-butyl-benzofuran-3-yl)-hydroxy-methyl]-biphenyl-4-ol;
4'-[(2-benzyl-benzo[b]thiophen-3-yl)-hydroxy-methyl]-biphenyl-4-ol;
(2-butyl-benzofuran-3-yl)-[5-(4-methoxy-phenyl)-oxazol-2-yl]-methanol;
(2-butyl-benzofuran-3-yl)-[5-(4-methoxy-phenyl)-oxazol-2-yl]-methanone;
2-(2-butyl-benzofuran-3-ymethyl)-5-(4-methoxy-phenyl)-oxazole;
[4-bromo-5-(4-methoxy-phenyl)-oxazol-2-yl]-(2-butyl-benzofuran-3-yl)-methanone;
4-bromo-5-(6-bromo-2-butyl-benzofuran-3-ylmethyl)-5-(4-methoxy-phenyl)-oxazole;
6-[(benzothiazol-2-ylsulfanyl)-(2-butyl-benzofuran-3-yl)-methyl]-naphthalen-2-ol;
4'-[(2-butyl-benzofuran-3-yl)-(benzothiazol-2-ylsulfanyl)-methyl]-biphenyl-4-ol;
2-[1-(benzo[b]thiophen-2-yl)-octylsulfanyl]-benzothiazole;
2-[(4-bromo-phenyl)-(2-butyl-benzofuran-3-yl)-methylsulfanyl]-benzothiazole;
2-[(4-bromo-naphthalen-1-yl)-(2-butyl-benzofuran-3-yl)-methylsulfanyl]-benzothiazole;
2-[(2-butyl-benzofuran-3-yl)-phenyl-methylsulfanyl]-benzothiazole;
[2,6-dibromo-4-(naphthalene-2-carbonyl)-phenoxy]-acetic acid;

5-[2,6-dibromo-4-(naphthalen-2-ylmethyl)-phenoxymethyl]-1H-tetrazole;

or a pharmaceutically acceptable salt or ester form thereof.

The compounds of this invention can be prepared as described in U.S. Pat. No. 6,110,963 (Malamas et al.—issued Aug. 29, 2000), the contents of which are incorporated herein by reference, or by other methods known in the art.

The compounds of this invention can be prepared according to the following schemes from commercially available starting materials or starting materials which can be prepared using to literature procedures. These schemes show the preparation of representative compounds of this invention.

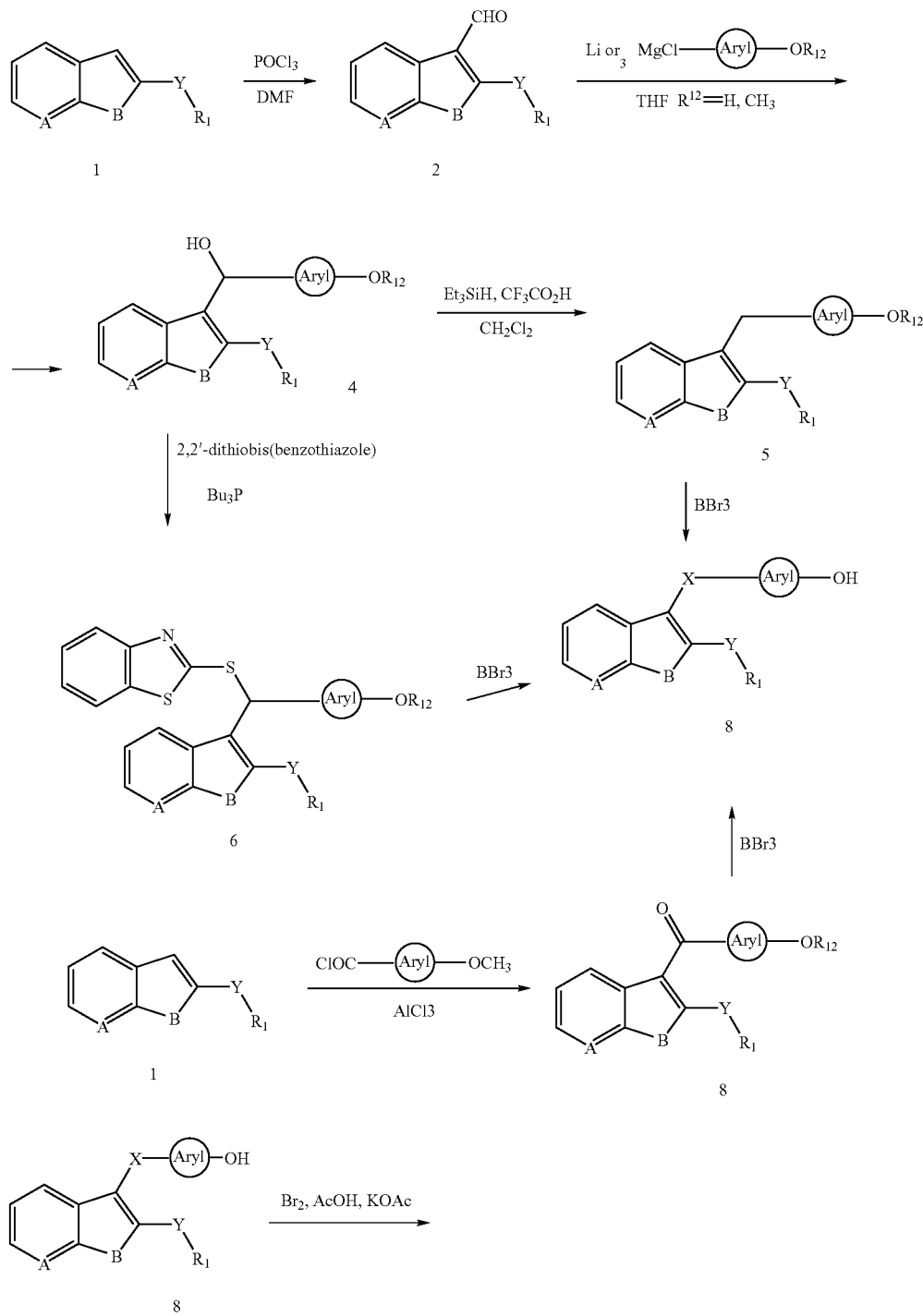

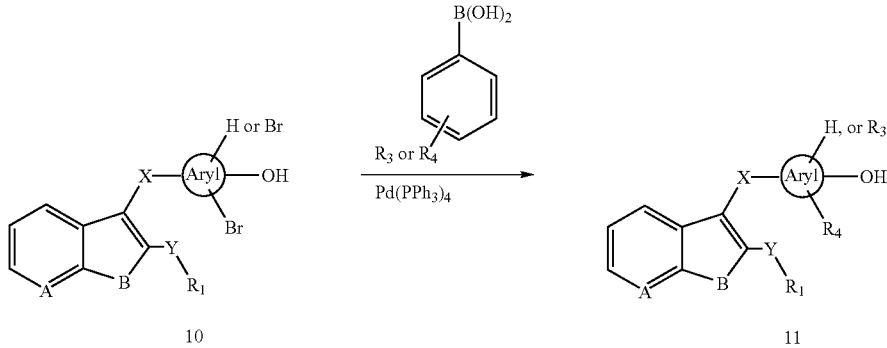

In Scheme I compounds (1) that are either commercially available or can be prepared by known methodologies from the 2-lithiated derivatives, obtained by treatment with alkyllithium reagents, of compounds (1) and the appropriate electrophiles Y—R[1] [ref. Org. React. 1979, volue 26]. Compounds (1) can be converted to 3-carboxaldehydes (2) upon treatment with phosphorus oxychloride and N,N-dimethylformamide [ref. Chim. Ther. 1996, 4, 221-227]. Aldehydes (2) can be treated with aromatic or heteroaromatic lithium (prepared by lithium halogen exchange, using for example n-BuLi) or Grignard reagents (3) to afford methyl-alcohols (4). Alcohols (4) can be reduced with triethylsilane/trifluoroacetic acid to produce (5) or can be converted to benzothiazoles (6) upon reaction with 2,2-dithiobis(benzothiazole) and tributylphosphine. Compounds (1) can also be converted to ketones (7) upon treatment with acyl chlorides and aluminum chloride [Friedel-Crafts and Related Reactions, Wiley Interscience, New York, 1963-1965]. Compounds (5), (6), and (7) can produce phenols (8) upon treatment with boron tribromide. Compounds (8) can be monobrominated or dibrominated (10) with bromine in the presence of potassium acetate and acetic acid. The brominated compounds (10) can be converted to terphenyl analogs (11) using the Suzuki protocol (arylboronic acids/palladium catalyst) [ref. Syn. Comm. 1981, 11, 513-519]. Compounds (10) and (11) can be treated with bromoacetonitrile in the presence of sodium hydride to give oxo-nitriles that can subsequently be converted to tetrazoles (14) upon treatment with sodium azide and ammonium chloride. Secondly, compounds (10) and (11) can be converted to the oxo-acetic acids (13) upon treatment with methyl bromoacetate, followed by saponification with sodium hydroxide. Thirdly, compounds (10) and (11) can be converted to carboxylic acids (12) by using the Mitsunobu protocol [ref. *Synthesis.* 1981, 1-27], for example, phenyllactic acid methyl ester, triphenylphosphine and diisopropyl azodicarboxylate. Conversion of either (10) or (11) to (12), (13) or (14) when X is —CH(OH)— will require the masking of the hydroxyl group, for example with a silyl reagent, followed by unmasking at the last step, for example with tetrabutylammonium fluoride.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure, stroke, peripheral arterial occlusion, and related disease states). These measures will slow the rate of progress of the disease state and assist the body in reversing the process direction in a natural manner.

Effective administration of these compounds may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

What is claimed:

1. A method for treatment of thrombosis in a mammal, the method comprising administering to a mammal in need thereof a pharmaceutically effective amount of a compound of formula I:

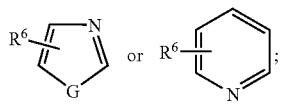

wherein
A is C;
B is O;
E is —X-D;
D is;

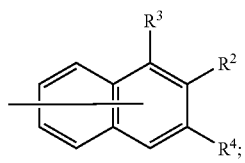

X is CO, CH(OH), CH$_2$, or —CH—S-2-benzothiazole;
Y is hydrogen, alkyl of 1-6 carbon atoms, or halogen;
Z is O, S, or N;
R is hydrogen, nitro, alkyl of 1-6 carbon atoms, alkoxy of 1-6 carbon atoms, halogen, or trifluoromethyl;
R$^1$ is alkyl of 1-12 carbon atoms, aryl of 6-10 carbon atoms, aralkyl of 7-15 carbon atoms, halogen, Het-alkyl wherein the alkyl moiety contains 1-6 carbon atoms, or aryl mono-, di- or tri-substituted with a substituent selected from the group consisting of halogen, alkyl of 1-6 carbon atoms, trifluoromethyl, and alkoxy of 1-6 carbon atoms;
Het is

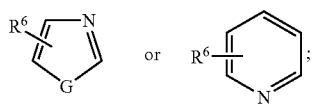

G is O, S, or N;
R$^2$ is hydrogen, halogen, alkyl of 1-6 carbon atoms, or —OR$^5$
R$^3$ and R$^4$ are each, independently, hydrogen, halogen, alkyl of 1-8 carbon atoms, aryl of 6-12 carbon atoms, nitro, amino, alkylsulfoamide, arylsulfoamide, cycloalkyl of 3-8 carbon atoms, heterocycle of 5 to 7 ring atoms containing from 1 to 3 heteroatoms selected from oxygen, nitrogen, or sulfur, or aryl of 6-10 carbon atoms mono-, di- or tri-substituted with a substituent selected from the group consisting of halogen, alkyl of 1-6 carbon atoms, trifluoromethyl, and alkoxy of 1-6 carbon atoms;
R$^5$ is hydrogen, alkyl of 1-6 carbon atoms, CH(R$^7$)R$^8$, —C(CH$_2$)$_n$CO$_2$R$^9$, —C(CH$_3$)$_2$CO$_2$R$^9$, CH(R$^7$)(CH$_2$)$_n$CO$_2$R$^9$, or —CH(R$^7$)C$_6$H$_4$CO$_2$R$^9$;
R$^6$ is alkylene of 1-3 carbon atoms;
R$^7$ is hydrogen, alkyl of 1-6 carbon atoms, aryl of 6-12 carbon atoms, aralkyl of 6-12 carbon atoms, cycloalkyl of 3-8 carbon atoms, phthalic acid, or Q-alkyl wherein the alkyl moiety contains 1-6 carbon atoms;
Q is

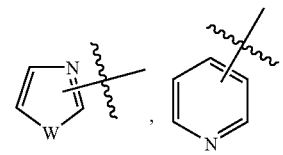

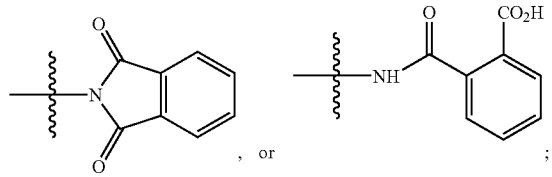

R$^8$ is —CO$_2$R$^{11}$, —CONHR$^{11}$, tetrazole, or —PO$_3$R$^{11}$;
R$^9$ is hydrogen, alkyl of 1-6 carbon atoms, aryl of 6-12 carbon atoms, or aralkyl of 7-15 carbon atoms;
W is O, N, or S;
R$^{11}$ is hydrogen, alkyl of 1-6 carbon atoms, aryl of 6-12 carbon atoms, or aralkyl of 7-15 carbon atoms;
n=1-6;
or a pharmaceutically acceptable salt or ester form thereof.

2. A method for the treatment of thrombosis or fibrinolytic impairment in a mammal wherein the thrombosis or fibrinolytic impairment is associated with formation of atherosclerotic plaques, venous and arterial thrombosis, myocardial ischemia, atrial fibrillation, deep vein thrombosis, pulmonary fibrosis, cerebral thrombosis, thromboembolic complications of surgery or peripheral arterial occlusion, the method comprising administering to a mammal in need thereof a pharmaceutically effective amount of a compound of formula I:

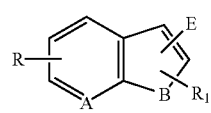

wherein
  A is C;
  B is O;
  E is —X-D;
  D is;

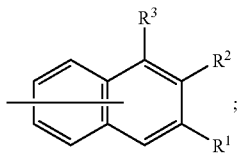

X is CO, CH(OH), CH$_2$, or —CH—S-2-benzothiazole;
Y is hydrogen, alkyl of 1-6 carbon atoms, or halogen;
Z is O, S, or N;
R is hydrogen, nitro, alkyl of 1-6 carbon atoms, alkoxy of 1-6 carbon atoms, halogen, or trifluoromethyl;
R$^1$ is alkyl of 1-12 carbon atoms, aryl of 6-10 carbon atoms, aralkyl of 7-15 carbon atoms, halogen, Het-alkyl wherein the alkyl moiety contains 1-6 carbon atoms, or aryl mono-, di- or tri-substituted with a substituent selected from the group consisting of halogen, alkyl of 1-6 carbon atoms, trifluoromethyl, and alkoxy of 1-6 carbon atoms;
Het is

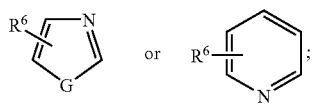

G is O, S, or N;
R$^2$ is hydrogen, halogen, alkyl of 1-6 carbon atoms, or —OR$^5$
R$^3$ and R$^4$ are each, independently, hydrogen, halogen, alkyl of 1-8 carbon atoms, aryl of 6-12 carbon atoms, nitro, amino, alkylsulfoamide, arylsulfoamide, cycloalkyl of 3-8 carbon atoms, heterocycle of 5 to 7 ring atoms containing from 1 to 3 heteroatoms selected from oxygen, nitrogen, or sulfur, or aryl of 6-10 carbon atoms mono-, di- or tri-substituted with a substituent selected from the group consisting of halogen, alkyl of 1-6 carbon atoms, trifluoromethyl, and alkoxy of 1-6 carbon atoms;
R$^5$ is hydrogen, alkyl of 1-6 carbon atoms, —CH(R$^7$)R$^8$, —C(CH$_2$)$_n$CO$_2$R$^9$, —C(CH$_3$)$_2$CO$_2$R$^9$, CH(R$^7$)(CH$_2$)$_n$CO$_2$R$^9$, or —CH(R$^7$)C$_6$H$_4$CO$_2$R$^9$;
R$^6$ is alkylene of 1-3 carbon atoms;
R$^7$ is hydrogen, alkyl of 1-6 carbon atoms, aryl of 6-12 carbon atoms, aralkyl of 6-12 carbon atoms, cycloalkyl of 3-8 carbon atoms, phthalic acid, or Q-alkyl wherein the alkyl moiety contains 1-6 carbon atoms;
Q is

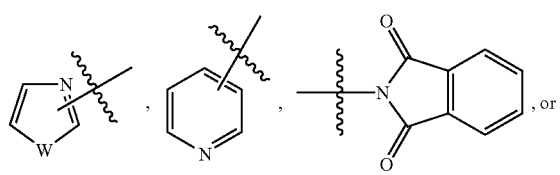, or

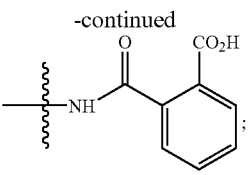

R$^8$ is —CO$_2$R$^{11}$, —CONHR$^{11}$, tetrazole, or —PO$_3$R$^{11}$;
R$^9$ is hydrogen, alkyl of 1-6 carbon atoms, aryl of 6-12 carbon atoms, or aralkyl of 7-15 carbon atoms;
W is O, N, or S;
R$^{11}$ is hydrogen, alkyl of 1-6 carbon atoms, aryl of 6-12 carbon atoms, or aralkyl of 7-15 carbon atoms;
n=1-6;
or a pharmaceutically acceptable salt or ester form thereof.

3. A method for the treatment of deep vein thrombosis in a mammal, comprising administering to a mammal in need thereof a pharmaceutically effective amount of a compound of formula I:

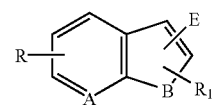    I wherein
  A is C;
  B is O;
  E is —X-D;
  D is;

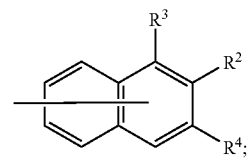

X is CO, CH(OH), CH$_2$, or —CH—S-2-benzothiazole;
Y is hydrogen, alkyl of 1-6 carbon atoms, or halogen;
Z is O, S, or N;
R is hydrogen, nitro, alkyl of 1-6 carbon atoms, alkoxy of 1-6 carbon atoms, halogen, or trifluoromethyl;
R$^1$ is alkyl of 1-12 carbon atoms, aryl of 6-10 carbon atoms, aralkyl of 7-15 carbon atoms, halogen, Het-alkyl wherein the alkyl moiety contains 1-6 carbon atoms, or aryl mono-, di- or tri-substituted with a substituent selected from the group consisting of halogen, alkyl of 1-6 carbon atoms, trifluoromethyl, and alkoxy of 1-6 carbon atoms;
Het is

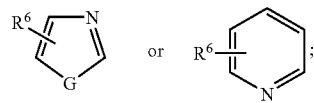

G is O, S, or N;

R² is hydrogen, halogen, alkyl of 1-6 carbon atoms, or —OR⁵

R³ and R⁴ are each, independently, hydrogen, halogen, alkyl of 1-8 carbon atoms, aryl of 6-12 carbon atoms, nitro, amino, alkylsulfoamide, arylsulfoamide, cycloalkyl of 3-8 carbon atoms, heterocycle of 5 to 7 ring atoms containing from 1 to 3 heteroatoms selected from oxygen, nitrogen, or sulfur, or aryl of 6-10 carbon atoms mono-, di- or tri-substituted with a substituent selected from the group consisting of halogen, alkyl of 1-6 carbon atoms, trifluoromethyl, and alkoxy of 1-6 carbon atoms;

R⁵ is hydrogen, alkyl of 1-6 carbon atoms, —CH(R⁷)R⁸, —C(CH₂)ₙCO₂R⁹, —C(CH₃)₂CO₂R⁹, CH(R⁷)(CH₂)ₙCO₂R⁹, or —CH(R⁷)C₆H₄CO₂R⁹;

R⁶ is alkylene of 1-3 carbon atoms;

R⁷ is hydrogen, alkyl of 1-6 carbon atoms, aryl of 6-12 carbon atoms, aralkyl of 6-12 carbon atoms, cycloalkyl of 3-8 carbon atoms, phthalic acid, or Q-alkyl wherein the alkyl moiety contains 1-6 carbon atoms;

Q is

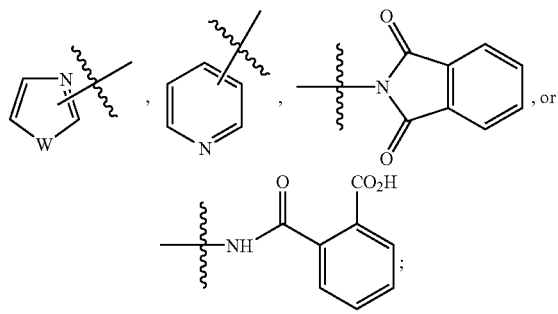

R⁸ is —CO₂R¹¹, —CONHR¹¹, tetrazole, or —PO₃R¹¹;

R⁹ is hydrogen, alkyl of 1-6 carbon atoms, aryl of 6-12 carbon atoms, or aralkyl of 7-15 carbon atoms;

W is O, N, or S;

R¹¹ is hydrogen, alkyl of 1-6 carbon atoms, aryl of 6-12 carbon atoms, or aralkyl of 7-15 carbon atoms;

n=1-6;

or a pharmaceutically acceptable salt or ester form thereof.

4. A method of claim 1 wherein the compound is:

6-[(2-butyl-benzofuran-3-yl)-hydroxy-methyl]-naphthalen-2-ol;
6-[(2-butyl-benzofuran-3-ylmethyl)]-naphthalen-2-ol;
1-bromo-6-(2-butyl-benzofuran-3-ylmethyl)-naphthalen-2-ol;
[1-bromo-6-(2-butyl-benzofuran-3-ylmethyl)-naphthalen-2-yloxy]-acetic acid; or
2-[1-bromo-6-(2-butyl-benzofuran-3-ylmethyl)-naphthalen-2-yloxy]-3-phenyl-propionic acid; or a pharmaceutically acceptable salt or ester form thereof.

5. A method of claim 1 wherein the compound is:

5-[1-bromo-6-(2-butyl-benzofuran-3-ylmethyl)-naphthalen-2-yloxymethyl]-1H-tetrazole;
6-(2-butyl-benzofuran-3-ylmethyl)-1-iodo-naphthalen-2-ol;
2-[-6-(2-butyl-benzofuran-3-ylmethyl)-1-iodo-naphthalen-2-yloxy]-3-phenyl-propionic acid;
1-bromo-6-[(2-butyl-benzofuran-3-yl)-hydroxy-methyl]-naphthalen-2-ol;
[1-bromo-6-(2-butyl-benzofuran-3-carbonyl)-naphthalen-2-yloxy]-acetic acid;
or a pharmaceutically acceptable salt or ester form thereof.

6. A method of claim 1 wherein the compound is:

2-[1-bromo-6-(2-butyl-benzofuran-3-carbonyl)-naphthalen-2-yloxy]-3-phenyl-propionic acid; or
[5-bromo-6-(1H-tetrazol-5-ylmethoxy)-naphthalen-2-yl]-(2-butyl-benzofuran-3-yl)-methanone;
or a pharmaceutically acceptable salt or ester form thereof.

7. A method of claim 3 wherein the compound is:

6-[(benzothiazol-2-ylsulfanyl)-(2-butyl-benzofuran-3-yl)-methyl]-naphthalen-2-ol; or
2-[(4-bromo-naphthalen-1-yl)-(2-butyl-benzofuran-3-yl)-methylsulfanyl]-benzothiazole;
or a pharmaceutically acceptable salt or ester form thereof.

8. A method of claim 3 wherein the compound is:

6-[(2-butyl-benzofuran-3-yl)-hydroxy-methyl]-naphthalen-2-ol;
6-[(2-butyl-benzofuran-3-ylmethyl)]-naphthalen-2-ol;
1-bromo-6-(2-butyl-benzofuran-3-ylmethyl)-naphthalen-2-ol;
[1-bromo-6-(2-butyl-benzofuran-3-ylmethyl)-naphthalen-2-yloxy]-acetic acid; or
2-[1-bromo-6-(2-butyl-benzofuran-3-ylmethyl)-naphthalen-2-yloxy]-3-phenyl-propionic acid; or a pharmaceutically acceptable salt or ester form thereof.

9. A method of claim 3 wherein the compound is:

5-[1-bromo-6-(2-butyl-benzofuran-3-ylmethyl)-naphthalen-2-yloxymethyl]-1H-tetrazole;
6-(2-butyl-benzofuran-3-ylmethyl)-1-iodo-naphthalen-2-ol;
2-[-6-(2-butyl-benzofuran-3-ylmethyl)-1-iodo-naphthalen-2-yloxy]-3-phenyl-propionic acid;
1-bromo-6-[(2-butyl-benzofuran-3-yl)-hydroxy-methyl]-naphthalen-2-ol;
[1-bromo-6-(2-butyl-benzofuran-3-carbonyl)-naphthalen-2-yloxy]-acetic acid;
or a pharmaceutically acceptable salt or ester form thereof.

10. A method of claim 3 wherein the compound is:

2-[1-bromo-6-(2-butyl-benzofuran-3-carbonyl)-naphthalen-2-yloxy]-3-phenyl-propionic acid; or
[5-bromo-6-(1H-tetrazol-5-ylmethoxy)-naphthalen-2-yl]-(2-butyl-benzofuran-3-yl)-methanone;
or a pharmaceutically acceptable salt or ester form thereof.

11. A method of claim 3 wherein the compound is:

6-[(benzothiazol-2-ylsulfanyl)-(2-butyl-benzofuran-3-yl)-methyl]-naphthalen-2-ol; or
2-[(4-bromo-naphthalen-1-yl)-(2-butyl-benzofuran-3-yl)-methylsulfanyl]-benzothiazole;
or a pharmaceutically acceptable salt or ester form thereof.

12. A method of claim 2 wherein the compound is:

2-[1-bromo-6-(2-butyl-benzofuran-3-carbonyl)-naphthalen-2-yloxy]-3-phenyl-propionic acid;
[5-bromo-6-(1H-tetrazol-5-ylmethoxy)-naphthalen-2-yl]-(2-butyl-benzofuran-3-yl)-methanone;
6-[(2-butyl-benzofuran-3-yl)-hydroxy-methyl]-naphthalen-2-ol;
6-[(2-butyl-benzofuran-3-ylmethyl)]-naphthalen-2-ol;
1-bromo-6-(2-butyl-benzofuran-3-ylmethyl)-naphthalen-2-ol;

1-bromo-6-(2-butyl-benzofuran-3-ylmethyl)-naphthalen-2-yloxy]-acetic acid;

2-[1-bromo-6-(2-butyl-benzofuran-3-ylmethyl)-naphthalen-2-yloxy]-3-phenyl-propionic acid;

5-[1-bromo-6-(2-butyl-benzofuran-3-ylmethyl)-naphthalen-2-yloxymethyl]-1H-tetrazole;

6-(2-butyl-benzofuran-3-ylmethyl)-1-iodo-naphthalen-2-ol;

2-[-6-2-butyl-benzofuran-3-ylmethyl)-1-iodo-naphthalen-2-yloxy]-3-phenyl-propionic acid;

1-bromo-6-[(2-butyl-benzofuran-3-yl)-hydroxy-methyl]-naphthalen-2-ol;

[1-bromo-6-(2-butyl-benzofuran-3-carbonyl)-naphthalen-2-yloxy]-acetic acid;

6-[(benzothiazol-2-ylsulfanyl)-(2-butyl-benzofuran-3-ylmethyl]-naphthalen-2-ol; or 2-[(4-bromo-naphthalen-1-yl)-(2-butyl-benzofuran-3-yl)-methylsulfanyl]-benzothiazole;

or a pharmaceutically acceptable salt or ester form thereof.

* * * * *

UNITED STATES PATENT AND TRADEMARK OFFICE
CERTIFICATE OF CORRECTION

PATENT NO. : 7,291,639 B2  Page 1 of 1
APPLICATION NO. : 10/171056
DATED : November 6, 2007
INVENTOR(S) : Hassan Mahmoud Elokdah It is certified that error appears in the above-identified patent and that said Letters Patent is hereby corrected as shown below:

In column 11, lines 20-25, Formula I, please replace

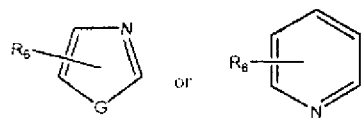

with:

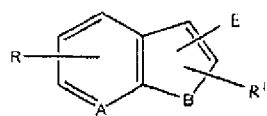

Signed and Sealed this

Twenty-third Day of September, 2008

JON W. DUDAS
*Director of the United States Patent and Trademark Office*